(12) United States Patent
Murata et al.

(10) Patent No.: US 6,459,002 B1
(45) Date of Patent: Oct. 1, 2002

(54) PROCESS FOR PREPARING CYCLOHEXANONE, CYCLOHEXANOL AND CYCLOHEXYL HYDROPEROXIDE

(75) Inventors: Shuzo Murata, Niihama (JP); Nobuhiro Tani, Niihama (JP)

(73) Assignees: Sumitomo Chemical Company, Limited, Osaka (JP); Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/992,012

(22) Filed: Nov. 26, 2001

(30) Foreign Application Priority Data

Nov. 24, 2000 (JP) ........................................ 2000-357363

(51) Int. Cl.[7] ...................... C07C 45/32; C07C 409/00; C07C 37/08
(52) U.S. Cl. ...................... 568/357; 568/389; 568/570; 568/802
(58) Field of Search ................................. 568/357, 389, 568/802, 320, 570

(56) References Cited

U.S. PATENT DOCUMENTS

| | | |
|---|---|---|
| 5,030,739 A | 7/1991 | Foricher et al. |
| 5,175,316 A | 12/1992 | Agar et al. |
| 5,780,683 A * | 7/1998 | Greene et al. |
| 5,981,420 A * | 11/1999 | Nakano et al. |

FOREIGN PATENT DOCUMENTS

| | | |
|---|---|---|
| EP | 0 579 323 | 1/1994 |
| JP | 8-38909 | 2/1996 |
| JP | 9-143109 | 6/1997 |

OTHER PUBLICATIONS

Patent Abstract of Japan Publication No. 2000–239210, published Sep. 5, 2000.

Y. Ishii et al., "Development of Novel Aerobic Oxidation Method of using N–Hydroxyphthalimide as Catalyst", Journal of Synthetic Organic Chemistry, Japan 57(1), 24, (1998), pp. 38–48.

T. Iwahama et al., "Direct Conversion of Cyclohexane into Adipic Acid with Molecular Oxygen Catalyzed by N–Hydroxypthalimide Combined with $Mn(acac)_2$ and $Co(OAc)_2$" Organic Process R&D, vol. 2, No. 4, (1998), pp. 255–260 with Abstract.

* cited by examiner

Primary Examiner—Johann Richter
Assistant Examiner—Sikarl A. Witherspoon
(74) Attorney, Agent, or Firm—Sughrue Mion, PLLC

(57) ABSTRACT

Cyclohexanone, cyclohexanol and/or cyclohexyl hydroperoxide are prepared at a high productivity by allowing cyclohexane to be in contact with an oxygen-containing gas using a catalyst comprising a cyclic N-hydroxyimide and a transition metal compound in the presence of cyclohexanone and optional cyclohexanol.

4 Claims, No Drawings

PROCESS FOR PREPARING CYCLOHEXANONE, CYCLOHEXANOL AND CYCLOHEXYL HYDROPEROXIDE

FIELD OF THE INVENTION

The present invention relates to a process for preparing cyclohexanone, cyclohexanol and cyclohexyl hydroperoxide.

BACKGROUND ART

Hitherto, cyclohexanone, cyclohexanol and/or cyclohexyl hydroperoxide are often prepared by oxidizing cyclohexane with molecular oxygen (hereinafter referred to as "oxygen" simply) in the production process of KA oil (a mixture of cyclohexanone and cyclohexanol), and the like.

In these years, an improved process for oxidizing cyclohexane with oxygen using a catalyst comprising an imide compound such as N-hydroxyphthalimide or a catalyst comprising such an imide compound and a metal compound has been developed. For example, JP-A-8-38909, JP-A-9-327626, JP-A-10-286467 and JP-A-11-349493 disclose a process for oxidizing cyclohexane in the presence of the above catalyst in an organic solvent under an oxidizing atmosphere. JP-A-9-87215 and JP-A-9-143109 disclose a process for oxidizing cyclohexane using the above catalyst in the absence of solvents while flowing air or a nitrogen-oxygen mixture gas.

However, the process disclosed in JP-A-8-38909, etc. has insufficient productivity because of a low volumetric efficiency, and it is not a satisfactory process from the view point of costs since the amount of the catalyst used is large. In the process disclosed in JP-A-9-87215, etc., the conversion of cyclohexane is insufficient.

SUMMARY OF THE INVENTION

An object of the present invention is to prepare cyclohexanone, cyclohexanol and/or cyclohexyl hydroperoxide at a high productivity.

As a result of the extensive study, it has been found that the oxidation reaction of cyclohexane is accelerated when the reaction is carried out with adding cyclohexanone to the mixture of cyclohexane, a catalyst and oxygen, and thus the above object is achieved, and the present invention has been completed.

Accordingly, the present invention provides a process for preparing cyclohexanone, cyclohexanol and/or cyclohexyl hydroperoxide which comprises conducting oxidation of cyclohexane with an oxygen-containing gas in a reaction system containing cyclohexane and a catalyst comprising a cyclic N-hydroxyimide and a transition metal compound, cyclohexanone being added to the reaction system while conducting the oxidation.

DETAILED DESCRIPTION OF THE INVENTION

In the process of the present invention, cyclohexane is oxidized by allowing it to be in contact with an oxygen-containing gas using a catalyst comprising a cyclic N-hydroxyimide and a transition metal in the presence of cyclohexanone, which is initially added.

Examples of the cyclic N-hydroxyimide include N-hydroxyphthalimide, N-hydroxynaphthalimide, N-hydroxymaleimide, N-hydroxysuccinimide, etc., each of which may optionally have at least one substituent.

Examples of the substituent include alkyl groups having 1 to 6 carbon atoms, preferably 1 to 3 carbon atoms, aryl groups having 6 to 18 carbon atoms, preferably 6 to 12 carbon atoms, halogen atoms (e.g. fluorine atom, chlorine atom, etc.), a nitro group, and so on.

Specific examples of the cyclic N-hydroxyimide include N-hydroxyphthalimide, N-hydroxychlorophthalimide, N-hydroxynitrophthalimide, N-hydroxynaphthalimide, N-hydroxychloronaphthalimide, N-hydroxymaleimide, N-hydroxysuccinimide, etc.

The cyclic N-hydroxyimides may be used as a mixture of two or more of them, if necessary.

The amount of the cyclic N-hydroxyimide to be used may be about 0.1% by mole or less, and is preferably about 0.05% by mole or less, and is more preferably about 0.01% by mole or less, based on the amount of cyclohexane. The amount of the cyclic N-hydroxyimide is preferably at least about 0.0001% by mole, and more preferably at least about 0.001% by mole, based on the amount of cyclohexane.

Examples of the transition metal element contained in the transition metal compound include cerium, titanium, vanadium, chromium, molybdenum, manganese, iron, ruthenium, cobalt, rhodium, nickel, copper, etc. Among them, cobalt, cerium, manganese ruthenium and copper are preferred. The transition metal compound may be oxides, organic acid salts, inorganic acid salts, halides, alkoxides, complexes such as acetylacetonates, oxoacids and their salts, isopolyacids and their salts, heteropolyacids and their salts, etc. The transition metal compounds may be used as a mixture of two or more of them, if necessary.

The amount of the transition metal compound to be used may be about 0.1% by mole or-less, and is preferably about 0.01% by mole, and is more preferably about 0.005% by mole, based on the amount of cyclohexane. The amount of the transition metal compound is preferably at least about 0.000001% by mole, and more preferably at least about 0.00001% by mole, based on the amount of cyclohexane.

The oxygen-containing gas may be oxygen, air, or oxygen or air diluted with inert gas such as nitrogen, helium, etc.

The concentration of oxygen in the oxygen-containing gas is preferably from about 5% by volume to about 30% by volume, and more preferably from about 10% by volume to about 25% by volume.

The amount of the oxygen-containing gas to be fed is preferably from about 1% by mole to about 50% by mole, and more preferably from about 1% by mole to about 20% by mole, in terms of the amount of oxygen, based on the amount of cyclohexane.

For example, the oxygen-containing gas may be fed by dispersing bubbles of the oxygen-containing gas in the mixture containing cyclohexane, the catalyst and cyclohexanone. In such a case, a gas inlet tube may be used, or gas-blowing pores are provided in the reactor which contains the mixture.

The size of the bubbles may be suitably adjusted. From the viewpoint of increase of the reaction rate, the diameter of the bubbles is made small and is preferably 1 mm or less.

In the present invention, cyclohexanone is added to the reaction system in addition to cyclohexane, the catalyst and the oxygen-containing gas. The presence of cyclohexanone in the reaction system can accelerate the oxidation reaction of cyclohexane and increase the productivity. In addition, since cyclohexanone has a high ability to dissolve the catalyst, the catalyst can be dissolved in cyclohexanone or a liquid containing cyclohexanone, so that the catalyst can be supplied with good workabiliy.

The amount of cyclohexanone to be added may be at least about 0.1 part by weight, and is preferably at least about 0.2 part by weight, per 100 parts by weight of cyclohexane. The amount of cyclohexanone is preferably about 10 parts by weight or less and more preferably about 5 parts by weight or less.

In addition, cyclohexanol may also be added to the reaction system. In such a case, cyclohexanol can be oxidized to form cyclohexanone simultaneously with the oxidation of cyclohexane. When cyclohexanol is added, the amount of cyclohexanol may be from about 0.1 part by weight to about 15 parts by weight, and is preferably from about 0.2 part by weight to about 10 parts by weight, per 100 parts by weight of cyclohexane.

Cyclohexanone to be added to the reaction system may be one obtained by the process of the present invention. For example, a mixture containing cyclohexanone, which has been prepared by the process of the present invention, can be returned to the reaction system.

Cyclohexanol which may optionally be added to the reaction system may be one prepared by the process of the present invention. For example, a mixture containing cyclohexanol, which has been prepared by the process of the present invention, can be returned to the reaction system.

The mixture containing cyclohexanone and/or cyclohexanol to be added to the reaction system may be a fraction or a still residue, which is resulted from distillation and separation of the reaction mixture.

Cyclohexane and the catalyst may be recovered from the reaction mixture and recycled to the reaction system. Whether the catalyst is recovered or not may be decided by taking the costs or other factors into consideration.

The reaction temperature may be from about 90° C. to about 160° C., and is preferably from about 120° C. to about 150° C. The reaction pressure may be from about 0.1 MPa to about 3 MPa, and is preferably from about 0.1 MPa to about 2 MPa.

The reaction time (or the residence time) may be from about 0.1 hour to about 4 hours, and is preferably from about 0.2 hour to about 2 hours.

From the viewpoint of operability and productivity, the reaction is preferably carried out by continuously supplying cyclohexane, the catalyst, the oxygen-containing gas, cyclohexanone and optional cyclohexanol to the reaction system while removing the reaction mixture and waste gas from the reaction system.

The concentration of oxygen in the waste gas may be from about 0.01% by volume to about 10% by volume, and is preferably from about 0.01% by volume to about 8% by volume, in view of a selectivity to the product and safety of the process.

A ratio of the oxygen concentration in the waste gas to that in the oxygen-containing gas to be supplied may be from about 0.0004 to about 0.5.

Post-treatment after the reaction includes filtration, concentration, washing, treatment with an alkali or an acid, etc. Two or more of these treatments may be combined, if necessary.

The treatment with an alkali can saponify esters of carboxylic acids such as adipic acid with cyclohexanol to regenerate cyclohexanol, and also convert cyclohexyl hydroperoxide to cyclohexanone and/or cyclohexanol.

The purification may be carried out by, for example, distillation.

According to the process of the present invention as described above, the oxidation reaction of cyclohexane is accelerated and thus cyclohexanone, cyclohexanol and/or cyclohexyl hydroperoxide are produced at a high productivity.

EXAMPLES

The present invention will be illustrated by the following Examples, which do not limit the scope of the invention in any way.

In the Examples, an oxygen-containing gas having an oxygen concentration of 5% by volume or 10.5% by volume was prepared by diluting an air with nitrogen gas. The oxygen-containing gas was blown in a reaction mixture with a gas-inlet tube. The gas was exhausted through a cooling tube, which was cooled with water at 8° C., and a pressure-control valve.

Cyclohexane, cyclohexanone, cyclohexanol and cyclohexyl hydroperoxide were analyzed by gas chromatography, and adipid acid was analyzed by ion chromatography. From the results of those analyses, the convertion of cyclohexane, the total yield of cyclohexanone, cyclohexanol and cyclohexyl hydroperoxide, and the yield of adipic acid were calculated.

Example 1

In a one liter glass autoclave, cyclohexane (252.5 g, 3 moles), N-hydroxyphthalimide (0.28 g, 0.002 mole), cobalt octate (0.016 g, 0.00005 mole), cyclohexanone (6.7 g) and cyclohexanol (6.7 g) were charged, and a pressure and a temperature were adjusted to 1.05 MPa and 130° C. respectively under a nitrogen atmosphere.

Into the mixture in the autoclave, the oxygen containing gas having an oxygen concentration of 5% by volume was blown for one hour at a rate of 400 ml/min. while maintaining the above pressure and temperature. Thereafter, the oxygen-containing gas was switched to an air which was blown at a rate of 100 ml/min. After that, the rate of the air blowing was gradually increased to 550 ml/min. At the same time as the switch of the oxygen-containing gas to the air, (i) cyclohexane containing 76 ppm by weight of cobalt octate and (ii) cyclohexane containing 0.05% by weight of N-hydroxyphthalimide, 12.4% by weight of cyclohexanone and 12.4% by weight of cyclohexanol both started to be added to the mixture at 4.0 g/min. and 1.0 g/min. respectively. Successively, the reaction mixture was removed from the autoclave at substantially the same rate as the supply rate of the whole supply liquid while maintaining the above pressure and temperature, and the reaction was continued for 5 hours with a residence time of 1 hour.

The average oxygen concentration of the waste gas was 3.1% by volume. In the whole supply liquid, the concentrations of cyclohexane, cyclohexanone, cyclohexanol, N-hydroxyphthalimide and cobalt octate were 95% by weight, 2.4% by weight, 2.4% by weight, 0.01% by weight (0.0056% by mole based on cyclohexane) and 61 ppm by weight (0.0016% by mole based on cyclohexane) respectively.

The removed reaction mixture was analyzed. The concentrations of cyclohexanone, cyclohexanol and cyclohexyl hydroperoxide were 5.2% by weight, 3.8% by weight and 0.1% by weight respectively, the conversion of cyclohexane was 5.4%, and the total yield of cyclohexanone, cyclohexanol and cyclohexyl hydroperoxide was 3.8% (a selectivity of 71.4%). The yield of adipic acid was 0.7% (a selectivity of 13.1%).

Example 2

In a one liter glass autoclave, cyclohexane (252.5 g, 3 moles), N-hydroxyphthalimide (0.28 g, 0.002 mole), cobalt octate (0.016 g, 0.00005 mole), cyclohexanone (6.8 g) and cyclohexanol (6.7 g) were charged, and a pressure and a temperature were adjusted to 1.05 MPa and 140° C. respectively under a nitrogen atmosphere.

Into the mixture in the autoclave, the oxygen containing gas having an oxygen concentration of 5% by volume was blown for one hour at a rate of 400 ml/min. while maintaining the above pressure and temperature. Thereafter, the oxygen-containing gas was switched to an air which was blown at a rate of 100 ml/min. After that, the rate of the air blowing was gradually increased to 700 ml/min. At the same time as the switch of the oxygen-containing gas to the air, (i) cyclohexane containing 76 ppm by weight of cobalt octate and (ii) cyclohexane containing 0.05% by weight of N-hydroxyphthalimide, 12.5% by weight of cyclohexanone and 12.2% by weight of cyclohexanol both started to be added to the mixture at 4.0 g/min. and 1.0 g/min. respectively. Successively, the reaction mixture was removed from the autoclave at substantially the same rate as the supply rate of the whole supply liquid while maintaining the above pressure and temperature, and the reaction was continued for 5 hours with a residence time of 1 hour.

The average oxygen concentration of the waste gas was 0.2% by volume. In the whole supply liquid, the concentrations of cyclohexane, cyclohexanone, cyclohexanol, N-hydroxyphthalimide and cobalt octate were 95% by weight, 2.5% by weight, 2.4% by weight, 0.01% by weight (0.0055% by mole based on cyclohexane) and 61 ppm by weight (0.0016% by mole based on cyclohexane) respectively.

The removed reaction mixture was analyzed. The concentrations of cyclohexanone, cyclohexanol and cyclohexyl hydroperoxide were 6.7% by weight, 5.0% by weight and 0.4% by weight respectively, the conversion of cyclohexane was 8.9%, and the total yield of cyclohexanone, cyclohexanol and cyclohexyl hydroperoxide was 6.7% (a selectivity of 74.9%). The yield of adipic acid was 0.6% (a selectivity of 7.5%).

Example 3

The reaction was carried out in the same manner as in Example 2 except that the amount of cobalt octate to be initially added to the autoclave was changed from 0.016 g to 0.008 g (0.00002 mole), the final blowing rate of the air was changed from 700 ml/min. to 500 ml/min., the concentration of cobalt octate in the cyclohexane, which started to be added at 4.0 g/min. at the same time as the switch from the oxygen-containing gas to the air, was changed from 76 ppm by weight to 37 ppm by weight. Here, the concentrations of cyclohexane, cyclohexanone, cyclohexanol, N-hydroxyphthalmide and cobalt octate in the whole supply liquid were 95% by weight, 2.5% by weight, 2.5% by weight, 0.01% by weight (0.0058% by mole based on cyclohexane) and 29 ppm by weight (0.00075% by mole based on cyclohexane) respectively.

The removed reaction mixture was analyzed. The concentrations of cyclohexanone, cyclohexanol and cyclohexyl hydroperoxide were 5.3% by weight, 3.9% by weight and 0.2% by weight respectively, the conversion of cyclohexane was 5.3%, and the total yield of cyclohexanone, cyclohexanol and cyclohexyl hydroperoxide was 3.8% (a selectivity of 73.9%). The yield of adipic acid was 0.6% (a selectivity of 12.1%).

Comparative Example 1

In a one liter glass autoclave, cyclohexane (252.5 g, 3 moles), N-hydroxyphthalimide (0.28 g, 0.002 mole), cobalt octate (0.016 g, 0.00005 mole) and cyclohexanol (13.4 g) were charged, and a pressure and a temperature were adjusted to 1.05 MPa and 130° C. respectively under a nitrogen atmosphere.

Into the mixture in the autoclave, the oxygen containing gas having an oxygen concentration of 10.5% by volume was blown for one hour at a rate of 400 ml/min. while maintaining the above pressure and temperature. Thereafter, the oxygen-containing gas was switched to an air which was blown at a rate of 200 ml/min. At the same time as the switch of the oxygen-containing gas to the air, (i) cyclohexane containing 76 ppm by weight of cobalt octate and (ii) cyclohexane containing 0.05% by weight of N-hydroxyphthalimide and 24.7% by weight of cyclohexanol both started to be added to the mixture at 4.0 g/min. and 1.1 g/min. respectively. Successively, the reaction mixture was removed from the autoclave at substantially the same rate as the supply rate of the whole supply liquid while maintaining the above pressure and temperature, and the reaction was continued for 5 hours with a residence time of 1 hour.

The average oxygen concentration of the waste gas was 7.2% by volume. In the whole supply liquid, the concentrations of cyclohexane, cyclohexanol, N-hydroxyphthalimide and cobalt octate were 94% by weight, 5.3% by weight, 0.01% by weight (0.0061% by mole based on cyclohexane) and 59 ppm by weight (0.0015% by mole based on cyclohexane) respectively.

The removed reaction mixture was analyzed. The concentrations of cyclohexanone, cyclohexanol and cyclohexyl hydroperoxide were 1.3% by weight, 5.3% by weight and 0.5% by weight respectively, the conversion of cyclohexane was 1.8%, and the total yield of cyclohexanone, cyclohexanol and cyclohexyl hydroperoxide was 1.6% (a selectivity of 87.9%). The yield of adipic acid was 0.1% (a selectivity of 6.1%).

What is claimed is:

1. A process for preparing cyclohexanone, cyclohexanol and/or cyclohexyl hydroperoxide which comprises conducting oxidation of cyclohexane with an oxygen-containing gas in a reaction system containing cyclohexane and a catalyst comprising a cyclic N-hydroxyimide and a transition metal compound, cyclohexanone being added to the reaction system while conducting the oxidation.

2. The process according to claim 1, wherein the cyclohexanone prepared by said process is used as cyclohexanone to be added to the reaction system.

3. The process according to claim 1, wherein cyclohexanol is added to the reaction system.

4. The process according to claim 3, wherein the cyclohexanol prepared by said process is used as cyclohexanol to be added to the reaction system.

* * * * *